United States Patent
Redel

(10) Patent No.: US 7,742,797 B2
(45) Date of Patent: Jun. 22, 2010

(54) DEVICE AND METHOD FOR INTRALUMINAL IMAGING FOR THE RECONSTRUCTION OF 3D IMAGE DATA SETS

(75) Inventor: Thomas Redel, Poxdorf (DE)

(73) Assignee: Siemens Aktiengesellschaft, Munich (DE)

( * ) Notice: Subject to any disclaimer, the term of this patent is extended or adjusted under 35 U.S.C. 154(b) by 515 days.

(21) Appl. No.: 11/478,509

(22) Filed: Jun. 29, 2006

(65) Prior Publication Data
US 2007/0038062 A1 Feb. 15, 2007

(30) Foreign Application Priority Data
Jun. 30, 2005 (DE) .................. 10 2005 030 647

(51) Int. Cl.
*A61B 5/05* (2006.01)
(52) U.S. Cl. ........................ 600/407; 600/433
(58) Field of Classification Search .......... 600/106, 600/109, 114, 117, 433, 434, 466, 585; 604/164.13, 604/302
See application file for complete search history.

(56) References Cited

U.S. PATENT DOCUMENTS

| 4,676,249 | A | * | 6/1987 | Arenas et al. | 600/434 |
| 4,819,620 | A | * | 4/1989 | Okutsu | 600/114 |
| 5,662,116 | A | * | 9/1997 | Kondo et al. | 600/462 |
| 5,830,145 | A | * | 11/1998 | Tenhoff | 600/463 |
| 6,134,003 | A | | 10/2000 | Tearney et al. | |
| 2004/0049095 | A1 | * | 3/2004 | Goto et al. | 600/107 |
| 2004/0122326 | A1 | * | 6/2004 | Nair et al. | 600/467 |

FOREIGN PATENT DOCUMENTS

DE 100 34 251 C1 9/2001

\* cited by examiner

*Primary Examiner*—Long V Le
*Assistant Examiner*—Saurel J Selkin

(57) ABSTRACT

The invention relates to a device and a method for intraluminal imaging. The device features an imaging instrument and a transport unit, with which the imaging instrument is moved in a lumen at a defined speed over a defined distance. The device further features a rigid, i.e. mechanically-stable singly or multiply curved guide pipe, which has an internal diameter matched to the external diameter of the imaging instrument to accommodate and guide the imaging instrument and is made from a material which is transparent for the radiation or to the waves used in imaging. The guide pipe features at least one marking detectable with the imaging at a known position on the guide pipe and is mechanically connectable to the transport unit. The device and the method make it possible in a simple manner to record a 3D image data set from the intraluminal recorded 2D sectional images.

16 Claims, 4 Drawing Sheets

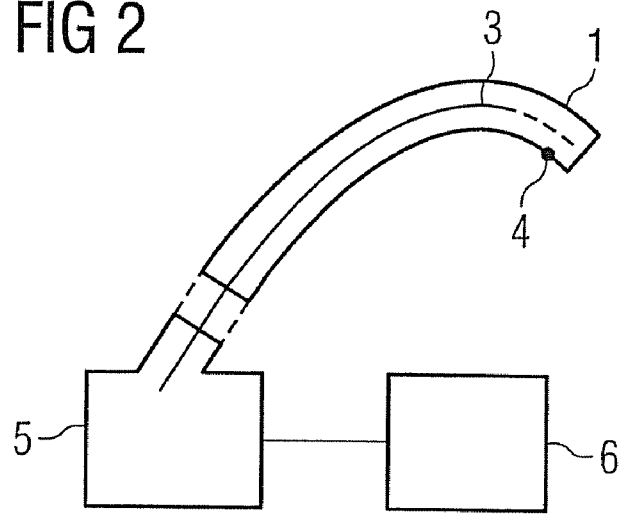
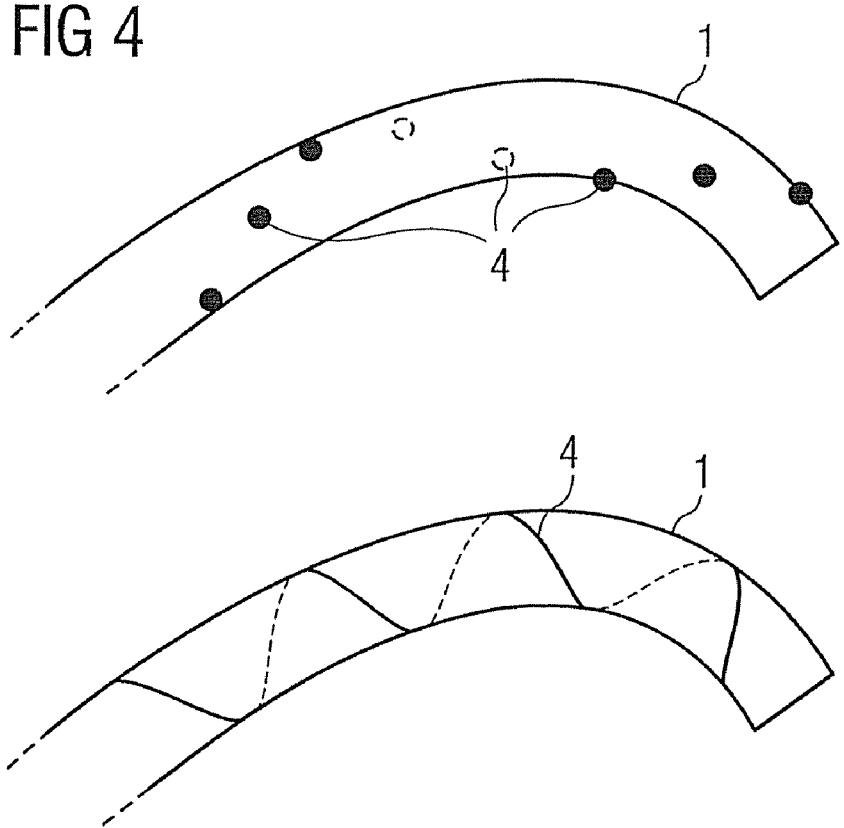

DEVICE AND METHOD FOR INTRALUMINAL IMAGING FOR THE RECONSTRUCTION OF 3D IMAGE DATA SETS

CROSS REFERENCE TO RELATED APPLICATIONS

This application claims priority of German application No. 10 2005 030 647.0 filed Jun. 30, 2005, which is incorporated by reference herein in its entirety.

FIELD OF THE INVENTION

The present invention relates to a device for intraluminal imaging which comprises an imaging catheter or an imaging endoscope as an imaging instrument for recording intraluminal cross-sectional images and a transport unit for the imaging instrument with which the imaging instrument can be pushed forwards and/or pulled back in a lumen at a defined speed over a defined distance. The invention also relates to a method for intraluminal imaging with such a device.

BACKGROUND OF THE INVENTION

The present device, as well as the associated method, above all relate to intraluminal imaging for medical applications, but can be used in other technical areas in which tomographic imaging data is to be obtained from a cavity or a hollow body. For this type of intraluminal imaging an imaging catheter or an imaging endoscope for recording intraluminal sectional images is introduced into the corresponding lumen. Thus for example, U.S. Pat. No. 6,134,003 A shows this type of imaging catheter, which creates the sectional images with the aid of optical coherence tomography (OCT). In medical applications layers of tissue can be recorded up to a specific depth of penetration of the radiation used with an imaging catheter of this type.

The processing of pulling the imaging catheter out of the lumen at a defined speed is known for the creation of sets of 3D images or of 3D images of the relevant hollow organ or cavity. This obtains a number of sectional images, from which, because of the known speed, a 3D image data set can be reconstructed.

For the three-dimensional reconstruction of cavities with a curved or wounded course from such a stack of two-dimensional sectional images however there is the problem of the individual sectional images not being able to be assembled in the correct spatial orientation to the three-dimensional image data set. The primary reason for this is that the exact position and orientation of the catheter tip and thereby the position of the image plane of each individual sectional image when the flexible catheter is used in curved or wounded cavities cannot be determined from the data obtained during imaging. The same problem occurs for principally similar problem definitions, such as for example the use of intraluminal ultrasound, confocal microscopy and/or the use of endoscopes instead of catheters.

The creation of a 3D image data record of a curved or wounded cavity or hollow organ has a role to play for example in the manufacturing of an insert, of an in-the-ear hearing aid for example, for the lumen of the auditory canal of a patient. To encompass the geometry of the inner ear a mold has previously been created which—after hardening and processing—is translated with a 3D scanner into a three-dimensional data set. However the production of such a mold is very uncomfortable for the patient. The entire process up to the point at which the three-dimensional data record is obtained, which is then used as the basis for creating the patient-individual insert, is a very complex one. There is therefore a need for a device and a method with which such a 3D image data record can be created in a simple manner.

A method is known from U.S. Pat. No. 5,830,145 A for reconstruction of 3D image data sets from intraluminal sectional images, which were recorded with an intraluminal ultrasound catheter (ILUS catheter). In this method special catheters are used which feature sensors on their tips. These enable the three-dimensional position and orientation of the catheter tip to be recorded at any time during the movement of the imaging catheter with a pullback unit. A three-dimensional track to which the individual sectional images are assigned is obtained from the 3D-position data. In this way a correct reconstruction of the 3D image data set can be obtained from the 2D sectional images. The execution of this intraluminal imaging however requires catheters with special position sensors as well as a corresponding tracking system.

A device for intraluminal imaging is known from U.S. Pat. No. 4,819,620, which comprises a rigid guide pipe made of a material which is transparent to the radiation used for imaging. The guide pipe has an internal diameter adapted to accommodate and guide an imaging instrument and at least one marking recognizable with imaging at a known position on the guide pipe.

SUMMARY OF THE INVENTION

The object of the present invention consists of specifying a device and also a method for intraluminal imaging, with which in a simple manner, especially without the use of an expensive tracking system, a three-dimensional image data set of the lumen can be created.

The object is achieved with the device as well as the method in accordance with the claims. Advantageous embodiments of the device as well as of the method are the object of the subclaims or can be taken from the subsequent description as well as from the exemplary embodiments.

The present device for intraluminal imaging features an imaging catheter or an imaging endoscope as its imaging instrument for recording intraluminal sectional images and a transport unit for the imaging instrument with which the imaging instrument can be pushed forwards and/or pulled back at a defined speed over a defined distance. Preferably this transport unit is a known pullback unit as is already known from the prior art in conjunction with the creation of intraluminal sectional image sequences. The outstanding feature of the present device is that a rigid, i.e. mechanically-stable singly or multiply curved guide pipe is provided, which has an internal diameter matched to the external diameter of the imaging instrument to accommodate and guide the imaging instrument and is made from a material which is transparent for the radiation used in imaging or for the waves used in imaging. The internal diameter of the opening of the guide pipe is in this case only minimally greater than the external diameter of the imaging instrument. The maximum allowed difference is produced by the maximum fault tolerances which must be adhered to for the intended intraluminal imaging. Optionally a transparent lubricant is also introduced between the inner wall of the pipe and the imaging instrument, to make it possible for the imaging instrument to move along the guide pipe with as little friction as possible.

The guide pipe features at least one marking which can be detected by the imaging at a known position on the guide pipe, and/or is mechanically connected to the transport unit. At least one of these two last-named features is required to obtain a registration between the guide pipe and the imaging instrument. If the guide pipe is fixed mechanically to the transport unit, there is automatically a registration with the imaging instrument since this is moved by the transport unit. The current position of the imaging part of the imaging instrument in the guide pipe is thus able to be determined at any time from the known movement of the imaging instrument with the transport unit. If the guide pipe is not connected to the transport unit, the registration between the guide pipe and the imaging instrument can be undertaken via the at least one marking on the guide pipe. Since this marking can be detected in at least one of the sectional images its exact position on the guide pipe is known, a fixed reference between the guide pipe and the imaging instrument is established in this manner. The exact position of the imaging part of the imaging instrument within the guide pipe, as a rule the tip of the imaging instrument, can thus be determined at any time, starting from this marking, using the known speed of the imaging instrument.

The marking on the guide pipe is in this case preferably arranged outside the area of the lumen to be detected with the image recording, for example, on the outermost distal end of the guide pipe, but must however be able to be recorded with the imaging instrument. In another embodiment the marking is designed to be so small that it does not disturb the image information in the sectional images but is still visible. A marking which is semitransparent in respect of the imaging can also be employed. The advantage of using of one or more markings on the guide pipe compared to the fixed mechanical attachment of the guide pipe to the transport unit is that different guide pipes, i.e. guide pipes of different lengths and/or different flexibility, and/or differently curved (bent), can be used without the expense of conversion, especially for different patients or applications.

The guide pipe in the present device is designed as a pipe with a single curve or with multiple curves, to enable corresponding cavities or hollow organs to be recorded. Preferably the device comprises a number of guide pipes for different dimensions or geometries of the cavities or hollow organs, for example for different patients. Different pipes for different dimensions or geometries may thus be of different lengths, different flexibility, and differently curved (bent). In an especially advantageous embodiment, the different guide pipes feature different markings, allowing them to be distinguished on the basis of the markings. Since with the subsequent reconstruction of the 3D image data set from the individual sectional images the exact three-dimensional track of the guide pipe used in the imaging must be known exactly, this guide pipe can be identified by an evaluation unit automatically on the basis of the markings in the sectional images in order in this manner to use the correct three-dimensional track as a basis for the 3D-image reconstruction. This three-dimensional track can for example be stored in an appropriate database with the different guide pipes which can be accessed by the evaluation unit.

The use of the present device and of the associated method is restricted to applications for which a corresponding rigid guide pipe can be introduced into the hollow organ or the cavity to be recorded. The guide pipe can be introduced for applications in the body of a patient for example, endoscopically into the lumen to be recorded, as far as this is possible. The calibration of the inner ear given as an application in the introductory description represents one example, into which a suitable curved, rigid guide pipe can easily be introduced. Should the guide pipe not be sufficiently well fixed during the image recording, i.e. during the pullback, in respect of the cavity to be calibrated, an additional fixing can be undertaken. In the case of the ear this can be done in a simple manner by a fixing with special plugs, preferably featuring a close-fitting through-opening for the guide pipe and inserted into the ear.

When the present method is carried out, the curved guide pipe is introduced into the lumen to be recorded and, if necessary, fixed in position in this lumen. Subsequently the imaging instrument is introduced into the guide pipe and pushed into the start position for the imaging. After the start of the imaging, in which as a rule at least a part of the imaging instrument rotates around the longitudinal axis of the imaging instrument, this is pulled back at a defined speed in the guide pipe with the transport unit. Since the guide pipe is transparent for the radiation used or the waves used in the imaging, the imaging can be carried out over the entire length of the guide pipe. A plastic or a glass can be used for example as materials for this type of transparent guide pipe in many cases. The guide pipe can in this case be embodied as a simple curved hollow needle.

The present device and the associated method are not restricted to a particular imaging technique. Instead different known imaging instruments can be used, for example, an OCT catheter as described in the known U.S. Pat. No. 6,134,003 A. Instead of the glass fiber articulation device used in this application it is also possible, to use the glass fiber directly with a fixed lens and mirror. A further example is the use of an ILUS catheter, as is known for example from U.S. Pat. No. 5,830,145 A which has also already been mentioned. Imaging instruments which use the technique of confocal optical tomography or other techniques to create sectional images can also be used in the present device. An example for the creation of sectional images with the technique or confocal optical tomography, also called confocal microscopy, can be found in DE 100 34 251 C1, the disclosure of which in respect of this imaging technique is included in the present description.

After the registration of the guide pipe and of the imaging instrument the recording positions of the individual sectional images in the guide pipe are known or at least able to be determined in a simple manner. The relevant orientation of the imaging instrument during image recording is thus also known from the knowledge of the three-dimensional track of the guide pipe. The 3D image data set can than be reconstructed with high accuracy from this data.

The imaging instrument and also the transport unit are controlled using a control and evaluation unit, which can take the form of a processor. This control and evaluation unit also performs the processing of the recorded image data, the registration of the guide pipe with the imaging instrument as well as the reconstruction of the 3D image data set from the recorded image data, taking into account the pullback speed as well as the three-dimensional track of the guide pipe.

If a non torsion-resistant imaging instrument is used, i.e. the imaging instrument is free to rotate about its longitudinal axis while in the guide pipe and being pulled back, it can be necessary to undertake the registration between the imaging instrument and the guide pipe at different positions in the guide pipe, i.e. at different pullback positions of the imaging instrument. Guide pipes with a number of markings distributed over the length of the guide pipe or one continuous marking can be used for this purpose, for example, a straight or spiral line which extends over the length of the guide pipe. This multiple registration, depending on the position at which the sectional images were recorded, means that deviations of the imaging instrument while it is being pulled back do not lead to an incorrect 3D reconstruction.

If this is necessary, the guide pipe can also feature additional markings which can be detected in an image of the body or of the organ in which the lumen to be calibrated is located recorded by external x-ray imaging or magnetic resonance tomography. A registration of the guide pipe with the body or with the organ itself can then be undertaken by an additional image recording of this type with the guide pipe introduced.

BRIEF DESCRIPTION OF THE DRAWINGS

The present device, as well as the associated method are explained again in greater detail below, on the basis an exemplary embodiment in conjunction with the drawings, without restricting the area of protection specified by the claims. The drawings show:

FIG. 2 an example for the present device shown in a schematic diagram;

FIG. 4 two examples for the embodiment or one or more markings along the guide pipe.

DETAILED DESCRIPTION OF THE INVENTION

In the present example a three-dimensional image data set of the volume of the auditory canal of a patient is recorded using optical coherence tomography (OCT). This is done using an imaging catheter 3, as is known for example from U.S. Pat. No. 6,134,003 A. Details of such an imaging catheter are thus not provided in this patent application.

In addition to the imaging catheter 3, the present device comprises a curved, rigid guide pipe 1 with known geometry. This guide pipe 1 features, as can be seen from the cross-sectional schematic diagram in Figure, an internal channel 2 which is matched in its diameter to the external diameter of the imaging catheter 3. In the present example the guide pipe 1 is made of a plastic material transparent for optical radiation, so that imaging with the imaging catheter 3 is made possible through the guide pipe. The guide pipe 1 is closed off at its distal end. This end is provided for safety with a soft, yielding material or is made of such a material in order to avoid injuries to the ear drum on introduction into the auditory canal of a patient.

Figure 1:
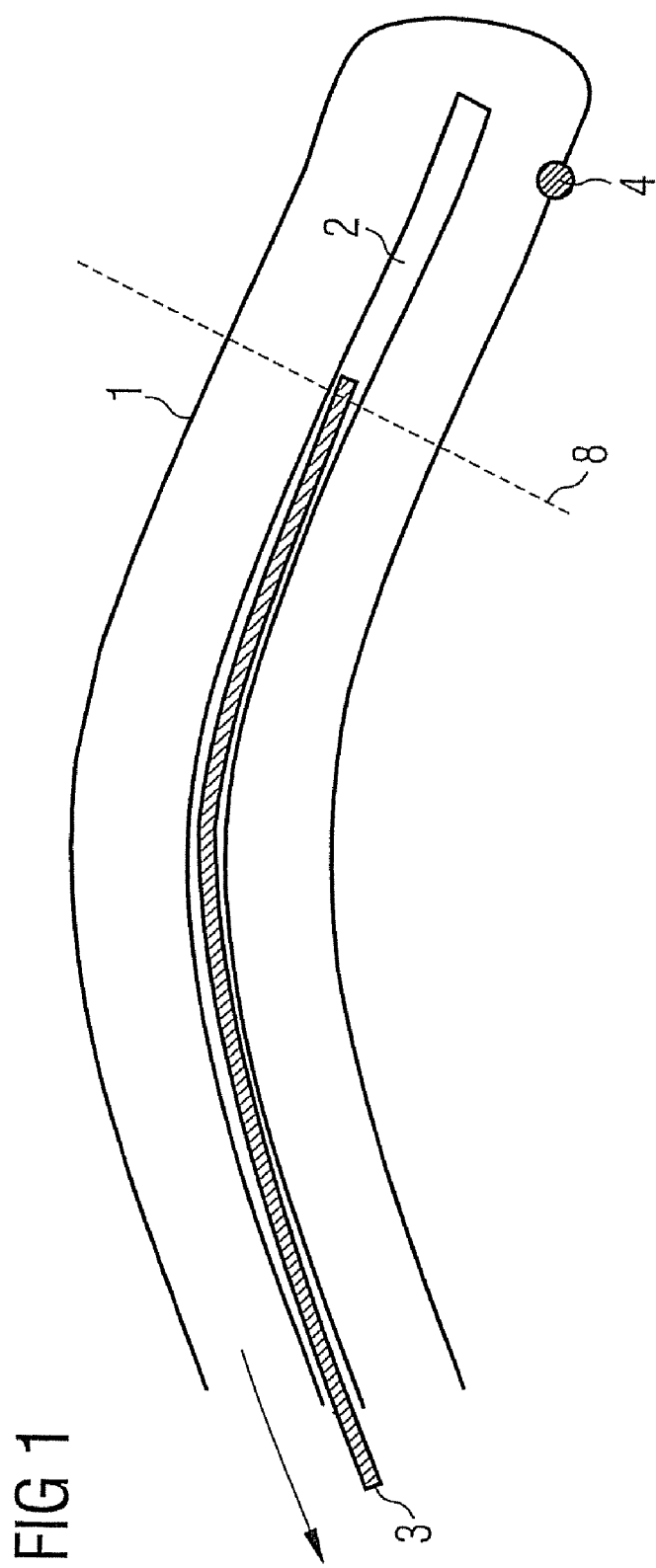
FIG. 1 an example of the guide pipe and the imaging instrument in a sectional schematic diagram.

FIG. 2 shows a highly schematicized representation of the basic structure of the present device. The imaging catheter 3 is in this case connected to a transport unit 5 which, in an embodiment, is a pullback unit, with which it can be pulled back in the guide pipe 1 at a defined, preferably constant speed during imaging. The pullback direction is indicated in FIG. 1 by the arrow. The guide pipe 1 can be rigidly mechanically connected to the transport unit 5, as indicated by the dashed line in FIG. 2. This is however not necessary in every case. Preferably the guide pipe instead has one or more markings 4 which are visible in the imaging, i.e. in at least one of the sectional images, and can thus be included for the registration between the imaging catheter 3 and the guide pipe 1. The imaging catheter 3 and the transport unit 5 are controlled via a control and evaluation unit 6, to which image data of the imaging catheter 3 is also fed for evaluation. The registration between imaging catheter 3 and guide pipe 1 based on the marking(s) 4 as well as the reconstruction of the 3D image data set from the image data of the recorded 2D sectional image is also undertaken by this control and evaluation unit 6.

When the method is carried out the curved guide pipe 1 is introduced into the auditory canal, with the distal, closed end as close as possible to the eardrum. Subsequently the imaging catheter 3 is introduced into the internal channel 2 of the guide pipe 1 and pushed with its image recording unit to the desired position. The imaging catheter 3 is constructed in this case so that the imaging is undertaken as close as possible to its distal tip. By rotating the holder unit of the imaging catheter 3 or, depending on embodiment, the entire imaging catheter 3, the corresponding sectional images are recorded. During this image recording the imaging catheter 3 is pulled back with the transport unit 5. During this pullback the imaging catheter 3 follows a defined path at a constant speed. This distance and the pullback speed are known, from which, after a registration of the imaging catheter 3 with the guide pipe 1, a fixed assignment of the recording position of the individual sectional images in relation to the guide pipe 1 is produced. The speed of rotation for the image recording should in this case be matched to the pullback speed.

The registration of the imaging catheter 3 and thereby of the sectional images with the guide pipe 1 is undertaken on the basis of the at least one marking 4 which is detectable in the sectional images. If necessary a registration with the ear anatomy can also be undertaken, as described in more detail below. On the basis of the registration with the known three-dimensional track of the guide pipe, the three-dimensional position and orientation are known for each sectional image, so that a correct 3D image data set of the recorded lumen can be created from the image data of the sectional images.

Figure 3:
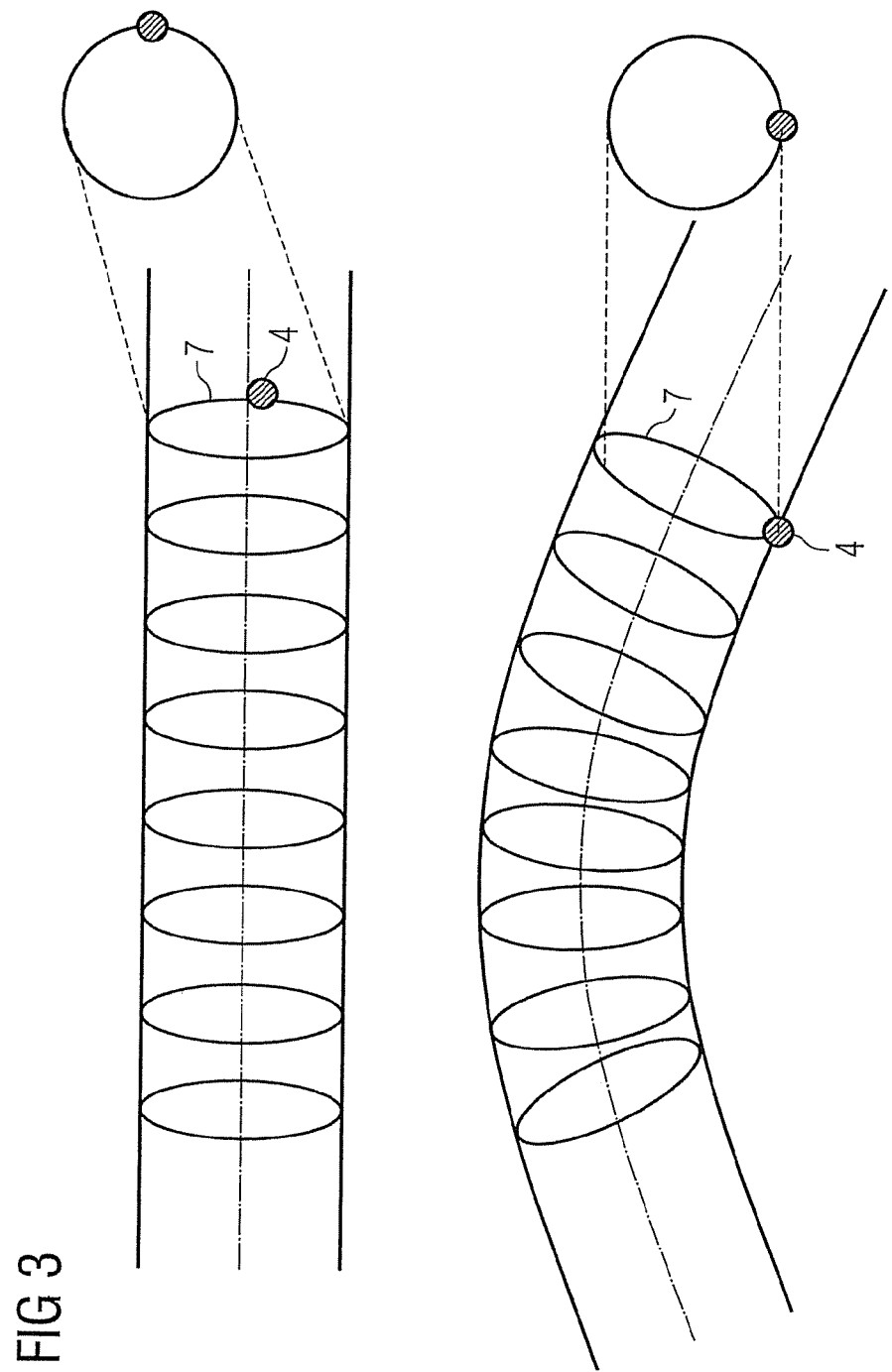
FIG. 3 a schematic diagram of the reconstruction of the 3D image data record from the sectional images.

To this end FIG. 3 is a schematic diagram showing at the top a number of sectional images 7 recorded in sequence (indicated by circles) which are arranged at the correct distance from each other in accordance with the known pullback speed. The marking 4 recognizable in the sectional images 7 allows this sectional image to be assigned in its position and orientation to the known three-dimensional track of the guide pipe, which is shown in the lower illustration. In this way all sectional images 7, as can be seen in the lower illustration, are arranged in the correct spatial assignment, so that a correct 3D image data set can be reconstructed.

A segmentation of the reconstructed volume of the inner ear can also be undertaken in the control and evaluation unit 6. The 3D image data set can then be used through conventional further processing for dimensioning the shell of an inner ear insert.

In addition it is possible to use the information from the tissue contained in the sectional images. This can be identified by a manual or automatic segmentation of the different tissue structures (bone/soft tissue) detectable in the sectional images. This tissue information can also be transferred in addition to the 3D image data record for the further processing of the shell, for example visualized as a color code. A color then shows areas for example in which bony structures lie close to the surface of the skin, whereas another color indicates the exclusively soft structures.

For an external registration of the guide pipe in relation to the ear anatomy there is on the one hand the option of always introducing and fixing the guide pipe in a defined position in relation to the anatomy. Alternatively, after fixing, a flexible marker can be attached at a defined point of the ear to the guide pipe which is then recorded in the image as well and is used for external registration. This is necessary if, for example, an external connection to the inner era insert is necessary and this connection must be at a defined position of the ear anatomy.

The present method thus offers a simple, direct and patient-friendly option of obtaining a three-dimensional image data set of the auditory canal.

Figure 5:
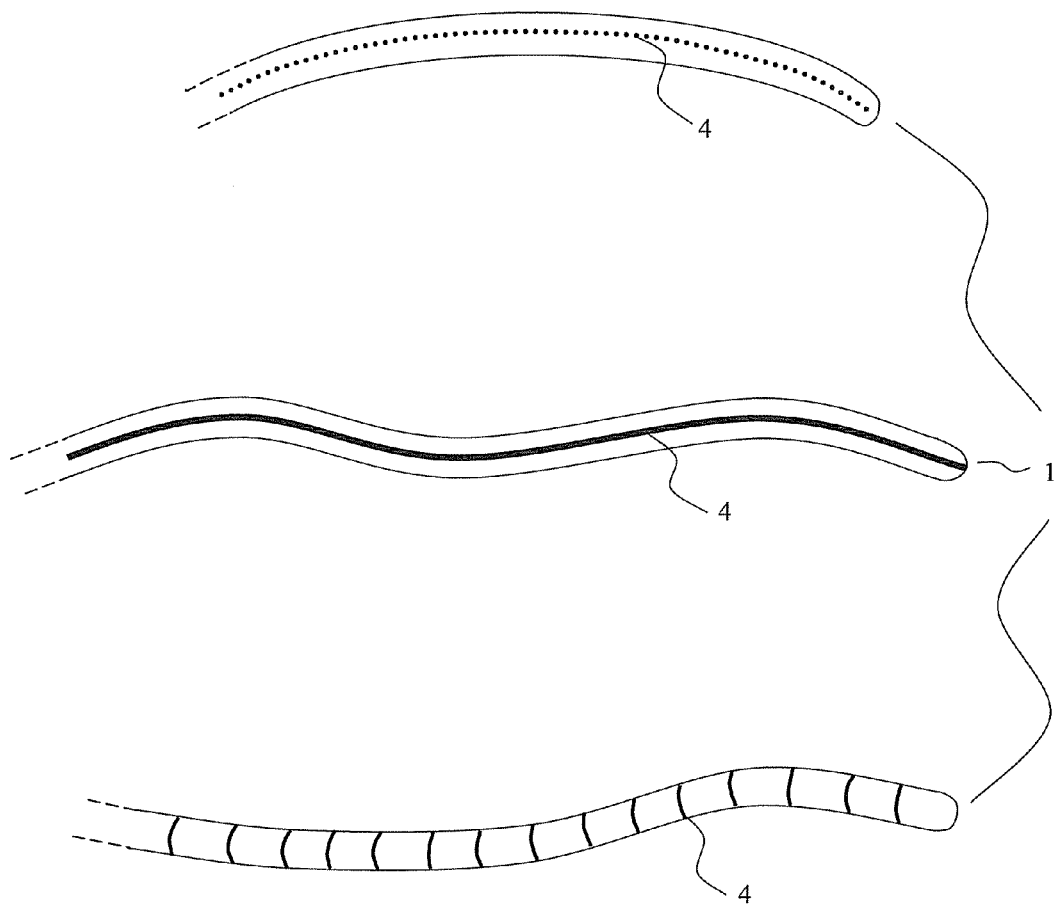
FIG. 5 a plurality of differently curved guide pipes with different markings.

Finally, FIG. 4 shows two more examples for the embodiment of markings 4 on the guide pipe. In one of the two illustrations the embodiment of a number of markings 4 over the length of the guide pipe 1 can be seen, while the other illustration shows a spiral line extending along the guide pipe 1 as the marking 4. FIG. 5 shows a plurality of differently curved guide pipes with a plurality of different markings used by the evaluation unit to identify the curved guide tube.

The invention claimed is:

1. A device for recording an intraluminal sectional image of a human medical patient, comprising:
   an imaging instrument for recording the intraluminal sectional image;
   a transport unit for moving the imaging instrument in a lumen of the patient at a defined speed over a defined distance;
   a guide pipe constructed and arranged for guiding the imaging instrument within the guide pipe, the guide pipe comprising:
      an internal, hollow, nonlinear path constructed and arranged to guide the imaging instrument, wherein a diameter of the internal hollow path is has a curved shape with an diameter matched to an external diameter of the imaging instrument,
      material which is transparent for a radiation or for a wave used in the recording, and
      a marking which is detectable at the recorded sectional image at a known position on the guide pipe; and
   a control and evaluation unit which carries out a registration of the imaging instrument with the guide pipe using the marking on the guide pipe which is visible in the sectional image.

2. The device as claimed in claim 1, wherein the guide pipe is rigid.

3. The device as claimed in claim 1, wherein the guide pipe has a plurality of markings which are detectable with the sectional image at a plurality of known positions on the guide pipe arranged along the guide pipe.

4. The device as claimed in claim 1, wherein the marking is a line with a known course along the length of the guide pipe.

5. The device as claimed in claim 1, wherein the device comprises a plurality of guide pipes with different nonlinear paths, wherein guide pipes with different nonlinear paths comprise distinguishing markings are distinguished at the sectional image.

6. The device as claimed in claim 1, wherein a distal end of the guide pipe is closed off and is made of a yielding material or coated with the yielding material.

7. The device as claimed in claim 1, wherein the transport unit is a pullback unit.

8. The device as claimed in claim 1, wherein the control and evaluation unit: further:
   controls the imaging instrument and the transport unit for recording the sectional image along the lumen,
   computes a sectional image data for the recorded sectional image,
   determines a recording position of the sectional image along the guide pipe by the registration of the imaging instrument with the guide pipe, and
   creates a three-dimensional image data set of the lumen from the sectional image data, the determined recording position of the sectional image and a known three-dimensional course of the guide pipe.

9. The device as claimed in claim 1, wherein the imaging instrument is an imaging endoscope.

10. The device as claimed in claim 1, wherein the imaging instrument is an imaging catheter selected from the group consisting of: an optical coherence tomography catheter, an intraluminal ultrasound catheter, and a confocal optical tomography catheter.

11. A device for recording an intraluminal sectional image of a human medical patient, comprising:
   an imaging instrument for recording the intraluminal sectional image;
   a transport unit connected to the imaging instrument for moving the imaging instrument in a lumen of the patient at a defined speed over a defined distance;
   a rigid guide pipe which is mechanically connected to the transport unit for guiding the imaging instrument within the guide pipe, the guide pipe comprising:
      an internal, hollow, nonlinear path constructed and arranged to guide the imaging instrument, wherein a diameter of the internal hollow path is matched to an external diameter of the imaging instrument, and
      material which is transparent for a radiation or for a wave used in the recording; and
   a control and evaluation unit which carries out a registration of the imaging instrument with the guide pipe using the marking on the guide pipe which is visible in the sectional image.

12. A method for reconstructing a three-dimensional image data set with an intraluminal sectional image of a human medical patient, comprising:
   introducing a guide pipe with a marking that is detectable in the sectional image into a lumen of the patient;
   inserting an imaging instrument into the guide pipe;
   recording the intraluminal sectional image of the lumen;
   carrying out a registration of the imaging instrument with the guide pipe using the marking on the guide pipe which is visible in the sectional image;
   moving the imaging instrument by a transport unit at a speed in the guide pipe during the recording;
   computing a sectional image data for the recorded sectional image;
   determining a recording position of the sectional image along the guide pipe from the moving speed based on the registration and the known three dimensional course of the guide pipe; and
   creating a three-dimensional image data set of the lumen from the sectional image data of the sectional image considering the recording position known from the three-dimensional track of the guide pipe.

13. The method as claimed in claim 12, wherein introducing a guide pipe with a marking that is detectable in the sectional image comprises introducing a guide pipe with a marking that is detectable in the sectional image and has a plurality of markings or a continuous marking along its length, and wherein carrying out a registration of the imaging instrument with the guide pipe using the marking on the guide pipe comprises carrying out a registration of the imaging instrument with the guide pipe using the marking on the guide pipe more than once as the imaging instrument moves through it.

14. The method as claimed in claim 12,
   wherein a plurality of differently bent guide pipes are used for a plurality of different applications or objects,
   wherein the differently bent guide pipes are distinguished based on a plurality of different markings assigned to the guide pipes, and
   wherein one guide pipe which is used for recording the sectional image is identified by an evaluation of a marking in the sectional image so that a correct three-dimensional course of the one guide pipe is used for creating the three-dimensional image data set.

15. The method as claimed in claim 12,
wherein an additional marking element is attached at a defined position to the guide pipe which is detected in an image of the object recorded by an external x-ray device or magnetic resonance tomography,
wherein a registration of the guide pipe with the object is undertaken by an additional image recorded with the external x-ray device or magnetic resonance tomography with the guide pipe introduced.

16. The method as claimed in claim 12, further comprising identifying, segmenting, and representing different types of tissues with a plurality of different colors.

* * * * *